US000002050H2

(19) United States

(12) Statutory Invention Registration (10) Reg. No.: US H2050 H

Santos et al. (43) Published: Oct. 1, 2002

(54) β-CARRAGEENAN, PROCESSES FOR ITS PREPARATION, AND USES THEREFOR

(75) Inventors: Gertrudes A. Santos, Honolulu, HI (US); Donald W. Renn, Glen Cove, ME (US); Lisa E. Dumont, Rockport, ME (US); Charles A. Parent, Saco, ME (US)

(73) Assignee: FMC Corporation, Phila., PA (US)

(21) Appl. No.: 07/703,556

(22) Filed: May 21, 1991

(51) Int. Cl.[7] ..... C08B 37/00; C07H 13/12

(52) U.S. Cl. ..... 536/114; 536/118

(58) Field of Search ..... 536/114, 118

(56) References Cited

PUBLICATIONS

*Enzyme Nomenclature*, Academic Press, San Diego, California, pp. 356–357 (1992) (month unavailable).*

*Websters New Collegiate Dictionary*, G. & C. Merriam Company, 1977 (month unavailable) pp. 585.*

*Webster's New International Dictionary of the English Language*, Merriam–Webster (1956) (month unavailable) pp. 2015.*

Greer et al., "Characterization of Hybrid (Beta–Kappa–Gamma) Carrageenan from *Eucheuma gelatinae* J. Agardh (Rhodophyta, Solieriaceae) Using Carrageenases, Infrared and $^{13}$C–Nuclear Magnetic Resonance Spectroscopy", Botanica Marina, XXVII:473–478 (1984).

Mollion, et al., "$^{13}$C NMR study of the heterogeneity of the carrageenan from Rissoella verruculosa (Bert.) J.Ag. (Rhodophtya)", Food Hydrocolloids, 1:413–421 (1987).

Shi et al., "$^{13}$C–NMR Spectroscopic Analysis of Carrageenans from Chinese Eucheuma Species" Oceanologia et Limnoligia Sinica, 18, 3:265–272 (1987).

Zablackis et al., "The Carrageenan of *Catenella nipae* Zanard., a Marine Red Alga" Botanica Marina, XXIX:319–322 (1986).

* cited by examiner

*Primary Examiner*—Michael J. Carone

*Assistant Examiner*—Aileen J. Baker

(74) *Attorney, Agent, or Firm*—Bruce M. Monroe; Ratner & Prestia

(57) ABSTRACT

Purified and substantially pure β-carrageenan and processes for their preparation. Purified β-carrageenan can be obtained from a marine macroalga containing β-carrageenan and/or a precursor thereof by the steps of:

A. where the macroalga contains a precursor of β-carrageenan, reacting the macroalga with an alkaline compound to convert the precursor to β-carrageenan, B. extracting carrageenan from the macroalga, C. treating the extracted carrageenan with an aqueous quaternary ammonium salt to form a precipitate and an aqueous solution, D. separating the solution from the precipitate, and E. isolating purified β-carrageenan from the solution.

Substantially pure β-carrageenan can be obtained from purified β-carrageenan by the further steps of:

F. forming a solution of purified β-carrageenan in water,

G. contacting the solution with an ion exchange agent that removes carrageenan which contains sulfate ester from the solution, H. removing the resulting solution from contact with the ion exchange agent, and I. isolating substantially pure β-carrageenan from the solution.

16 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

β-CARRAGEENAN, PROCESSES FOR ITS PREPARATION, AND USES THEREFOR

BACKGROUND OF THE INVENTION

1. Field of the Invention

β-carrageenan, which is understood to be the idealized, nonsulfated member of the carrageenan family and the D,D-stereoisomer of agarose, consists of multiple units of carrabiose. Carrabiose contains 1,3-linked β-D-galactopyranose and 1,4-linked 3,6 anhydro α-D-galactopyranose units. β-carrageenan has been reported to occur in segments of natural carrageenans from marine macroalgae, but has never been isolated in pure or even in purified form where the sulfate ester content is less than 2% by weight.

2. Statement of Related Art

In an article by Greer et al., "Characterization of Hybrid (Beta-Kappa-Gamma) Carrageenan from *Eucheuma gelatinae* J. Agardh (Rhodophyta, Solieriaceae) Using Carrageenases, Infrared and $^{13}$C-Nuclear Magnetic Resonance Spectroscopy", Botanica Marina, XXVII:473–478 (1984), components of carrageenan from *Eucheuma gelatinae* were identified, including the presence of β-carrageenan and γ-carrageenan (a 6-sulfate precursor of β-carrageenan) using analytical techniques such as infrared and $^{13}$C-nuclear magnetic resonance, and the use of carrageenases.

Mollion et al., "$^{13}$C NMR study of the heterogeneity of the carrageenan from *Rissoella verruculosa* (Bert.) J. Ag. (Rhodophtya)", Food Hydrocolloids, 1:413–421 (1987) conducted a $^{13}$C-NMR study of carrageenan obtained from *Rissoella verruculosa* and obtained several fractions using fractionation techniques. All fractions contained relatively high levels of sulfate, and Mollion, et al. make it clear that they could not separate β- from ω-carrageenan by DEAE Sephadex® fractionation. See page 420, second paragraph under Table III.

Shi et al., "$^{13}$C-NMR Spectroscopic Analysis of Carrageenans from Chinese Eucheuma Species", Oceanologia et Limnoligia Sinica, 18, 3:265–272 (1987), in English translation, determined the compositions and structures of carrageenans without purification (including β-hybrids) from several species of Eucheuma using $^{13}$C-NMR spectroscopic analysis.

Zablackis et al., "The Carrageenan of *Catenella nipae* Zanard., a Marine Red Alga", Botanica Marina, XXIX:319–322 (1986), identified carrageenan from the red alga *Catenella nipae* Zanard as α-carrageenan in which the 1,4-linked units consist entirely of 3,6- anhydrogalactose 2-sulfate and the 1,3-linked galactose units are not sulfated, and illustrates structures of the "β- family".

Summary of the Invention

Processes have now been discovered for the preparation of both purified β-carrageenan, i.e. β-carrageenan containing from 1% to less than 2% by weight of sulfate ester, and substantially pure β-carrageenan, i.e. β-carrageenan containing less than 1% by weight of sulfate ester.

Purified β-carrageenan can be prepared by reacting a marine macroalga that contains β-carrageenan and/or a precursor thereof with an alkaline compound to convert a precursor present to β-carrageenan, extracting carrageenan from the macroalga, treating the extracted carrageenan with an aqueous quaternary ammonium salt to form a precipitate and an aqueous solution, separating the solution from the precipitate, and isolating purified β-carrageenan from the solution.

The substantially pure β-carrageenan is obtained from the above purified carrageenan by treating an aqueous solution of purified carrageenan with an insoluble ion exchange agent that selectively removes the more highly sulfate ester-containing carrageenans from the solution, and extracting substantially pure β-carrageenan from the solution remaining after separation of the ion exchange agent.

This invention also comprises purified and substantially pure β-carrageenan per se.

DETAILED DESCRIPTION OF THE INVENTION

Other than in the operating examples, or where otherwise indicated, all numbers expressing quantities of ingredients or reaction conditions used herein are to be understood as modified in all instances by the term "about".

Carrageenan, which is typically obtained by the aqueous reagent extraction of marine macroalgae such as *Chondrus crispus,* is a mix of polysaccharide fractions, differing in the amount and/or position of sulfate ester and/or other substituent groups they contain. Iota- carrageenan is the most highly sulfated member of the family. Lambda-carrageenan contains D-galactose and 35% ester sulfate. Kappa-carrageenan contains D-galactose and 3,6-anhydro-D-galactose and 25% ester sulfate. Gamma-carrageenan is the 6-sulfated precursor of β-carrageenan.

β-carrageenan, as discussed above, in its ideal form is a sulfate free member of the carrageenan family, and has not heretofore been isolated in either pure or purified form.

Processes have now been discovered for the preparation of both purified and pure β-carrageenan. When the term "purified β-carrageenan"is used herein, it is understood to mean β-carrageenan which contains from 1% to less than 2%, and preferably less than 1.75%, by weight of sulfate ester. The term "pure β-carrageenan" is β-carrageenan wherein less than 1% sulfate ester, and preferably less than 0.85% sulfate ester is present therein.

One process for the preparation of purified carrageenan from a marine macroalga containing β-carrageenan and/or a precursor thereof, comprises the following steps:

A. where the macroalga contains a precursor of β-carrageenan, reacting the macroalga with an alkaline compound to convert the precursor to β-carrageenan, B. extracting carrageenan from the macroalga, C. treating the extracted carrageenan with an aqueous quaternary ammonium salt to form a precipitate and an aqueous solution, D. separating the solution from the precipitate, and E. isolating purified β-carrageenan from the solution.

The macroalgae that can be employed in the above process include all marine macroalgae that contain either β-carrageenan, a precursor of β-carrageenan, or both. Macroalgae that contain relatively large quantities of β-carrageenan and/or a precursor thereof are preferred since the yields of purified β-carrageenan are thereby enhanced. *Eucheuma gelatinae* was found to be particularly suitable, although other macroalga such as *Eucheuma speciosa* for example can also be employed herein. The present invention is not limited to the use of any particular marine macroalga, provided only that the macroalga contains β-carrageenan and/or a precursor thereof.

The use of the term "a precursor of β-carrageenan" and like terms used herein are understood to mean β-carrageenan fractions that can be converted to β-carrageenan by the first steps of the process, i.e. by reaction of the macroalga with an alkaline compound. Gamma-carrageenan for example is such a β-carrageenan precursor. Gamma-carrageenan is O-α-D-galactopyranosyl- 6-sulfate (1→3) -O-β-D-galactopyranosyl (1→4).

Step A of the above process is normally carried out since most if not all marine macroalgae that meet the above criteria for use in the present process contain both β-carrageenan and a precursor thereof. However, in the event a macroalga is found that contains β-carrageenan without any precursor, step A can be omitted.

Step A is advantageously carried out in an aqueous medium at a temperature in the range of 50° C. to the boiling point of the mixture, and preferably at a temperature in the range of 75° C. to 95° C. The alkaline compound used in step A is preferably an alkali metal hydroxide, NaOH and KOH being most preferred. However, other more or less strongly alkaline compounds can also be employed such as an alkali metal borohydride in combination with an alkali metal hydroxide, alkaline earth metal hydroxides, ammonium hydroxide, mono-, di- and tri-alkyl and/or aryl substituted ammonium hydroxides, hydroxylamines, and the like. Examples of alkaline earth metal hydroxides are calcium hydroxide and barium hydroxide. Examples of mono-, di-, and tri- alkyl and/or aryl substituted ammonium hydroxides include the $C_1$–$C_6$ mono-, di-, and tri-alkyl ammonium hydroxides such as methyl ammonium hydroxide, dimethylammonium hydroxide, triethylammonium hydroxide, etc. Examples of hydroxylamines include $C_2$–$C_6$ hydroxyalkylamines, e.g. hydroxyethylamine, hydroxypropylamine, etc. The alkaline compound, e.g. the alkali metal hydroxides, can be present in from 5% (w/v) up to 40% (w/v) or more, preferably in the range of 20% to 30%. Treatment times are dependent on the hydroxyl ion concentration and the reaction temperature. For example, when concentrated alkali metal hydroxides are used at a temperature of 85° C. a treatment time of 1–6 hours, 2–4 hours is generally sufficient. However, when a temperature of 50° C. is employed, a longer treatment time of up to 72 hours is generally required. Similarly, the use of a weaker base such as ammonium hydroxide will require longer treatment times at a given temperature than are needed when alkali metal hydroxides are employed.

The macroalga used in step A can optionally be milled, e.g. in a Waring™ blender, prior to use.

Step B, i.e. the extraction of carrageenan from the macroalga, can be carried out by first separating the macroalga from the aqueous alkaline solution used in step A by any convenient means, such as pouring the suspension from step A over a strainer or filter, and then washing the macroalga with water until the wash water is only mildly alkaline, e.g. pH 8–9. The macroalga is then heated in hot to boiling water, preferably distilled water, or in hot dilute aqueous KCl solution, to extract the carrageenan, followed by filtration. Alternatively, the alkaline suspension from step A can be treated with an acid, e.g. acetic acid, until the suspension is neutral or mildly alkaline, and then isolating the macroalga followed by heating it in hot to boiling water.

Advantageously, the macroalga remaining after extraction is milled, for example in a Waring blender, and the resulting paste heated in hot to boiling water and filtered. The filtrates are then combined. The filtrates containing the carrageenan are preferably added to an excess of a water-miscible organic solvent, e.g. a $C_1$–$C_3$ alkanol such as methanol, ethanol, n- propanol and isopropyl alcohol, t-butyl alcohol, acetone, methyl ethyl ketone, and the like, to form a precipitate. The precipitate is separated and dried.

The extracted carrageenan from step B is then treated in step C with an aqueous quaternary ammonium salt to form a precipitate and an aqueous solution. Step C is preferably carried out by first dissolving the extracted carrageenan in hot water, and then adding an aqueous solution of a quaternary ammonium salt to the hot carrageenan solution. The quaternary ammonium salt precipitates the more highly sulfated components of the carrageenan, leaving a β-carrageenan enriched material containing less highly sulfated components in solution. The solution is separated from the precipitate, e.g. by filtration (step D).

Advantageously, the above treatment and filtration is repeated at least once, i.e. the separated precipitate is added to hot water, a solution of a quaternary ammonium salt is added thereto, and the resulting precipitate filtered off.

The filtrates are combined and purified β-carrageenan isolated therefrom (step E), e.g. by mixing the filtrates with an excess quantity of a water-miscible organic solvent to precipitate the purified β-carrageenan.

The quaternary ammonium salt used in step C is preferably benzethonium chloride (commercially available as Hyamine™ 3500 or Hyamine 1622 from Rohm & Haas, Phila., Pa.) or methylbenzethonium chloride (Hyamine 10X, Rohm & Haas). Other quaternary ammonium compounds can also be used, provided they selectively precipitate the more highly sulfated carrageenan components.

Alternatively, instead of the above described process, carrageenan can be extracted from the macroalga prior to treatment with an alkaline compound, i.e. step B is carried out prior to step A and the extracted carrageenan is treated with an alkaline compound to convert the precursor of β-carrageenan present therein to β-carrageenan. The remaining steps C–E are then the same as above.

Substantially pure β-carrageenan is extracted from purified β-carrageenan obtained from the above processes by the further steps of:

F. forming a solution of the purified β-carrageenan in water,

G. contacting the solution with an ion exchange agent that removes carrageenan components that contain sulfate ester from the solution, H. removing the resulting solution from contact with the ion exchange agent, and I. isolating substantially pure β-carrageenan from the solution.

In step F the purified β-carrageenan is preferably dissolved in hot water.

The ion exchange agent employed in step G is preferably diethylaminoethyl cellulose (DEAE-cellulose), epichlorohydrin triethanolamine cellulose (ECTEOLA- cellulose), or QAE-cellulose. However, any ion exchange agent which is insoluble in the solution or device containing same and which preferentially removes sulfate ester-containing carrageenan components from the solution while leaving β-carrageenan in solution can be employed in this step, such as agarose and cross-linked dextran cellulose analogs, and insoluble partially deacylated chitin.

Step H is preferably carried out by filtering off the ion exchange agent.

Step I is preferably carried out by precipitating the substantially pure β-carrageenan by addition of a water-miscible organic solvent. This solvent precipitation step can be carried out one or more times, and also optionally can be employed prior to step F.

Carrageenan and sulfate ester-containing fractions thereof known to the prior art are used as food emulsifiers and stabilizers, and as protective colloids in cosmetics and pharmaceutical preparations, e.g. as gelling agents and viscosity builders.

β-carrageenan is a neutral or nearly neutral gel former, and hence, in addition to the above uses, can be employed wherever such gels are desired. For example, it has been found that both the purified and the substantially pure β-carrageenan can be used in gel form for DNA electrophoresis, and will exhibit faster migration rates than agarose. Other uses for neutral or nearly neutral gelling agents include immunoassay media, protein separation media, chromatography media, microbial growth media, cell encapsulation media, and the like.

Pure β-carrageenan has a gelling temperature of 33° C. and a melting temperature of 70° C.

The invention will be illustrated but not limited by the following examples.

EXAMPLES

EXAMPLE 1

Purified β-carrageenan was isolated from the marine macroalga, *Eucheuma gelatinae,* by covering 20 g of the dried seaweed with 400 ml of 20% (w/v) potassium hydroxide. To complete the conversion of the 6-sulfated galactose segments to 3,6-anhydro galactose units, the suspension was heated without agitation for three hours at 85° C., using a water bath. The modified seaweed was recovered by pouring the suspension over a strainer. The retained seaweed was rinsed with continuously replaced cold water. Washing was continued until the pH of the wash was 8 to 9. Usually 2 to 3 hours is required. The modified seaweed was transferred to a beaker containing 500 ml of 30% (w/v) sodium chloride and allowed to soak overnight to ion-exchange from $K^+$ to $Na^{++}$. The ion-exchanged seaweed was washed with cold water as above to remove excess salts, then heated with distilled water in a boiling-water bath for 1 hour at 95° C. After 1 hour, the water/seaweed mixture was allowed to cool slightly and then milled in a Waring™ blender 7010 (model #31BL91). The resulting paste was returned to the boiling-water bath at 95° C. for another hour. The pH of the paste was checked and adjusted with 1M acetic acid to maintain the pH between 8 and 9. To this, 30 g of filter aid was added, stirred, and the mixture filtered using a 1 liter filter bomb fitted with a piece of #50 Whatman™ filter paper. The collected and combined filtrate and wash were heated to 70° C. and, with stirring, added to 2x volume of 99% isopropyl alcohol warmed to 40° C. The coag was recovered by pouring through finely woven nylon cloth and squeezing to remove excess alcohol. To wash the coag, it was allowed to stand in 1x volume of 80% isopropyl alcohol for 30 minutes. The coag was recovered as above, squeezed to remove excess alcohol, and dried at 55° C. in a forced hot-air oven. Once dried, the sample was weighed. 7.59 g (38% yield) was recovered and then ground through a 20 mesh screen. To isolate the β-carrageenan, the dried product was dissolved in 759 ml distilled water (1% w/v), using heat. While hot (40° C.), 114 ml of 5% Hyamine™ 3500 quaternary ammonium salt solution (Rohm & Haas, Philadelphia, Pa.), 15% v/v, was added to the extract and then the mixture placed in a boiling-water bath for 20 minutes. The precipitate which formed was separated by centrifugation at 4000 rpm for 10 minutes. A small portion of the clear supernatant solution was checked for additional precipitables by adding a few drops of Hyamine 3500 solution. If and when more precipitate formed, additional Hyamine solution was added to the total volume of the supernatant and centrifuged again as above to remove the precipitate. To the clear supernatant containing the β-carrageenan, 10% aqueous sodium chloride was added at 1% of the total volume. The solution was heated to 70° C. in a microwave oven and after which it was added, with stirring, to 2x volumes of 99% isopropyl alcohol that was warmed to 40° C. After several hours, a floc formed. The coag was collected by vacuum filtration through #50 Whatman™ filter paper. The coag was dried at 50° C. Once dried, the recovered sample weighed 0.287 g (1.44%, based on the weight of the weed used). The dried product was ground through a 20 mesh screen. A sample of this product was analyzed. The product contained 13.14% by weight moisture, 2.73% by weight ash (750° C. in a platinum crucible), 1.73% by weight sulfate ester, no free sulfate, 0.002% by weight $Mg^{++}$, 0.10% by weight $Na^+$, 35.98% by weight of anhydrogalactose, essentially no kappa- or iota-carrageenan fragments, a gelling temperature of 31° C., and a melting temperature of 63° C. A 1% aqueous solution was prepared from this product, using heat. Upon cooling at room temperature a strong, clear gel formed.

EXAMPLE 2

The process of Example 1 was repeated. However, following grinding of the dried product through a 20 mesh screen, the ground product was dissolved in distilled water (1%) with heating and then coagulated in 2x volume of 99% isopropyl alcohol. The coag was recovered by filtering through finely woven nylon cloth. The excess alcohol was removed by squeezing, then dispersed in 30% isopropyl alcohol. The warm coag began to dissolve in the 30% isopropyl alcohol. Therefore, a few drops of 30% sodium chloride was added to reprecipitate the β-carrageenan. The precipitate was recovered as in Example 1 by filtration and redissolved in distilled water using heat. The sample was then recoagulated in 99% isopropyl alcohol containing a few drops of 30% sodium chloride and collected by filtration. This coag was then washed in 30% isopropyl alcohol for 30 minutes. The coag was recovered by centrifugation at 2500 rpm for 10 minutes. The alcohol was removed by decantation and the coag washed in 200 ml 2% sodium chloride with 0.25% tetrasodium ethylene diaminetetraacetic acid (EDTA) solution for 30 minutes. The coag was centrifuged at 2500 rpm for 10 minutes and then washed in 350 ml distilled water for 30 minutes. The coag was washed for 30 minutes each in 30% and 40% isopropyl alcohol, recovering the coag as above. The coag was then hardened in 350 ml 99% isopropyl alcohol for 30 minutes and recovered on a finely woven nylon cloth, squeezing to remove excess alcohol. The coag was dried in a forced-air oven overnight at 45° C. The dried product was ground through a 20 mesh screen. This product was dissolved in 400 ml distilled water with heat. While hot, 65 ml of 5% Hyamine 3500 solution was added, making the solution cloudy. To this solution a small amount of filter aid was added and then filtered in a filter bomb precoated with filter aid. The filtrate was collected and coagulated in 2x volume of 99% isopropyl alcohol. The coag was washed in a series of washes as above recovering the coag between washes by centrifugation at 2500 rpm for 10 minutes. The washed coag was then hardened in 99% isopropyl alcohol and squeezed to remove excess alcohol. The coag was dried at 45° C. overnight and then ground through a 20 mesh screen. Gels from this product were comparable to gels formed from β-carrageenan from Example 1.

EXAMPLE 3

The process of Example 1 was repeated except for the following: After the 20% potassium hydroxide treatment at 85° C. for 3 hours, the seaweed was washed with cold water, soaking the seaweed in water overnight in the refrigerator. The washed seaweed was then dried at 60° C. This dried seaweed was suspended in distilled water and heated in a boiling-water bath. This seaweed was pasted and filtered with filter aid as in Example 1, and then 5% Hyamine 3500 solution was added directly at 15% of the total volume. This solution was refiltered and coagulated as in Example 1. The dried product yield was 0.084 g (0.42%). The quality of this product was similar to that of Example 1.

EXAMPLE 4

The process of Example 2 was repeated except that 5% Hyamine 3500 solution was added to the pasted seaweed solution at 15% of the total volume and was then heated in a boiling waterbath for 20 minutes. After 20 minutes, filter aid was added and then filtered in the filter bomb. The filtrate was coagulated as in Example 2. After the coag was dried, the coag weighed 0.194 g (0.97%).

EXAMPLE 5

The process of Example 1 was repeated except that 5% Hyamine 3500 solution was added directly to the pasted seaweed before filtering with filter aid. The product yield was 0.036 g (0.18%). The product obtained from this procedure was similar to that obtained in Example 1.

EXAMPLE 6

The process of Example 5 was repeated except that 5% Hyamine solution was added to the filtrate of the filtered paste. The product yield was 0.134 g (0.6%).

EXAMPLE 7

*Eucheuma gelatinae* (20 g) was suspended in 400 ml distilled water and the pH of the solution was adjusted with 1.0 N NaOH to 7.0–8.0. The solution was heated to 95° C. in a microwave oven, transferred to a boiling waterbath, and further heated with occasional stirring for 3 hours. The pH of the solution was monitored every 30 minutes. After 3 hours, the seaweed was milled in a Waring™ blender and the pH adjusted if necessary to 7.0–8.0. The paste was then diluted to 900 ml with distilled water, 30 g of filter aid added, and the paste filtered through a filter bomb. The collected filtrate was coagulated in 2x volume 99% isopropyl alcohol and recovered as in Example 1. The coag was dried at 60° C. and then ground through a 20 mesh screen. The ground coag was dissolved by dispersing in 600 ml distilled water, then heating to a boil. Using an exhaust hood, 5.983 of sodium borohydride (lot #784162, Fisher Scientific, Fair Lawn, N.J.) was added, with 1-octanol as an antifoaming agent to reduce foaming. This solution was transferred to a boiling waterbath and heated to 95° C. for 20 minutes. An equal volume of 20% KOH (600 ml) was added and the solution heated to 95° C. for 2 hours. After 2 hours, the pH was adjusted with acetic acid to 8.0–9.0. The solution was then coagulated in 2x volume 99% isopropyl alcohol. The coag was washed in 80% isopropyl alcohol, recovering the coag between washes and drying the coag at 60° C. The dried coag was ground and then dissolved in distilled water with heat. To the hot solution, 5% Hyamine 3500 solution was added at a level equal to 15% of the total volume, then the mixture was heated in a boiling-water bath for 2 minutes. Filter aid (15 g) was added and the solution pressure filtered using a preheated filter bomb. The collected filtrate was checked with extra Hyamine solution as above and remained clear. The filtrate was then coagulated in 2x volume 99% isopropyl alcohol with 10% NaCl added at 1% of the total volume. The coag was recovered and washed in 60% isopropyl alcohol. After the coag was hardened in 99% isopropyl alcohol, it was dried at 60° C. The dried coag weighed 0.862 g, a 4.3% yield. Analysis of this material gave similar results to the product from Example 1.

EXAMPLE 8

20 g of *Eucheuma gelatinae* seaweed was suspended in 400 ml distilled water and the pH adjusted with 1.0 N NaOH to 7.0–8.0. This solution was heated to 95° C. for 3 hours. The hot solution was diluted with distilled water and filtered in a preheated filter bomb with filter aid. The collected filtrate was coagulated in 2x volume 99% isopropyl alcohol. The coag was shredded in a Waring blender and added to an additional 500 ml 99% isopropyl alcohol. To this 500 ml of 30% NaOH solution was added and then heated to 85° C. in a waterbath for 2 hours. After 2 hours, the solution was neutralized with 3M acetic acid and glacial acetic acid and then coagulated in 2x volume 99% isopropyl alcohol. The alcohol was removed by decantation and 60% isopropyl alcohol added as a wash. Again, the alcohol was removed and 99% isopropyl alcohol added to the residue, the mixture stirred to effect equilibration, and the coag recovered by centrifugation at 2500 rpm for 10 minutes. The pellet was dried at 60° C. The dried material was ground and dissolved in 1500 ml distilled water with heat. While hot, 5% Hyamine 3500 solution was added, the mixture filtered using filter aid, and the filtrate coagulated in 2x volume 99% isopropyl alcohol. The coag was recovered and washed, then dried at 60° C. The recovered β-carrageenan weighed 0.997 g, a 4.99% yield. There were no significant differences observed in this product compared to that of Example 1.

EXAMPLE 9

To prepare substantially pure β-carrageenan, one gram of β-carrageenan prepared as described in Example 1 was suspended in 100 ml distilled water and heated with constant stirring to dissolve the β-carrageenan (70° C.). This 1% w/v β-carrageenan solution was cooled to 40° C. With constant stirring, a solution of n-alkyl (50% $C_{14}$, 40% $C_{12}$, 10% $C_{16}$) dimethyl benzyl ammonium chloride (FMB 451-5 QUAT, Huntington Laboratories, Huntington, Ind.) was added at a level (3 ml) of 3x the milli-equivalents of sulfate in β-carrageenan. This solution was incubated at 37° C., a temperature higher than that at which β-carrageenan gels. After 2 hours of incubation, additional FMB 451-5 QUAT solution was added to check for more flocculation. The mixture was then heated to 40° C. To this, with stirring, 3 g Hyflo Super-Cel filter aid (Manville Service Corporation, Lompoco, Calif.) was added. This slurry was then poured into a 100 ml pressure filter bomb, containing a piece of #50 Whatman filter paper previously coated with 8 g filter aid and preheated with 100 ml boiling distilled water. Pressure was applied (25 psi or about 1,760 g/cm$^2$), the filtrate collected, then maintained at a temperature of 40° C. The filter cake was rinsed with 100 ml hot distilled water and this wash was combined with the primary filtrate. This solution was then coagulated in 2x volume (400 ml) 99% isopropyl alcohol. To check for residual β-carrageenan in the filter aid cake, the aid cake was rinsed with an additional 50 ml hot distilled water and the filtrate poured into 100 ml 99% isopropyl alcohol. No coagulum formed in the isopropyl alcohol. The coagulated β-carrageenan was allowed to cool to room temperature (20° C.) and recovered by centrifugation at 3500 rpm for 10 minutes. The supernatant was removed by decantation. The pellet was transferred to and dispersed in 2x volume (400 ml) 60% isopropyl alcohol. After 30 minutes, the coagulum was recovered on a fine woven cloth by vacuum filtration. Excess alcohol was removed by squeezing. The coagulum was washed in 2x volume 2% aqueous sodium chloride (w/v) for 30 minutes. The coagulum was filtered as above, squeezing out excess liquid and then the coagulum was washed in 2x volume distilled water for 30 minutes. The coagulum was recovered as above, and then hardened in 2x volume 99% isopropyl alcohol for 30 minutes. The coagulum was again filtered, squeezed to remove excess alcohol and then was dried overnight (16 hours) in an airdraft incubator at 37° C. Once dried, the sample was weighed to determine yield, typically about 50%. In this experiment, 0.512 g (51.2%) was obtained. This was then ground through a 40 mesh screen. A 1% solution was then prepared in distilled water and heated to 70° C. to dissolve the β-carrageenan. A 2.5% slurry of DEAE cellulose was also prepared by suspending 1.25 g DEAE cellulose (lot # 68F-0744, Sigma Chemical Co., St. Louis, Mo.) in 50 ml distilled water and stirring for 10 minutes. The DEAE cellulose powder was recovered on a piece of #54 Whatman filter paper by vacuum filtration. The washed DEAE cellulose powder was added to the β-carrageenan solution and the mixture allowed to stir at about 37° C. After 2 hours, the DEAE cellulose was removed by vacuum filtration using a piece of #54 Whatman filter paper. The DEAE cellulose was rinsed with 50 ml hot distilled water and the filtrate mixed with the previously filtered β-carrageenan. The β-carrageenan was then coagulated in 2x volume (200m) 99% isopropyl alcohol. The coagulum was collected on a finely woven nylon cloth by vacuum filtration and then transferred to 2x volume (200 ml) 60% isopropyl alcohol. After 30 minutes, the coagulum was again recovered on a finely woven cloth and the excess alcohol removed by squeezing. The coagulum was then hardened in 2x volume 99% isopropyl alcohol for 30 minutes. The coagulum was again recovered and then dried overnight at 37° C. A 60.8% yield (0.304 g) was obtained. A 1% aqueous solution prepared from the product obtained from this protocol exhibited very little metachromasia when Toluidine Blue was added and formed a firm opaque gel. An electroendoosmosis (EEO) value of $-m_r=0.31$ was obtained. The dried product was analyzed with the following results (all percentages are percent by weight unless otherwise noted)—15.75% moisture, 1.50% ash, 0.84% ester sulfate, no free sulfate, 0.07% $Cl^-$, no $Mg^{++}$, no $Ca^{++}$, 0.2% $K^+$, 0.21% $Na^+$, 0.01% pyruvate, 38.24% anhydrogalactose, an optical rotation value (specific rotation value) of +68.6 using the sodium D line (589 nm) at 60° C. with a 1.5% w/v solution, filtered to 0.45$\mu$, a gel temperature of 33° C., and a melting temperature of 70° C. IR and NMR spectra confirmed both the carrageenan backbone and the essential absence of kappa- and iota-carrageenan fragments.

EXAMPLE 10

The process of Example 9 was repeated except that the non β-carrageenan precipitate from the addition of FMB 451-5 QUAT solution was removed by centrifugation at 3500 rpm for 10 minutes. The clear supernatant was coagulated and washed as in Example 9. After drying at 37° C., the β-carrageenan was weighed to calculate yield, which in this case was 0.55 g (55%). This material was ion-exchanged as above and the yield was 89.6%. Analysis of this material indicated that it was similar to that obtained in Example 9.

EXAMPLE 11

β-carrageenan was isolated from the marine macroalga, *Eucheuma gelatinae,* by covering 20 g of the dried seaweed with 400 ml of 20% (w/v) potassium hydroxide. The suspension was heated in a 50° C. waterbath without agitation for three days. The modified seaweed was recovered by pouring the suspension over a strainer. The retained seaweed was rinsed with continuously replaced cold water. Washing was continued until the pH of the wash was 8 to 9 (2 to 3 hours). The modified seaweed was transferred to a beaker containing 500 ml of 30% (w/v) sodium chloride and allowed to soak overnight to ion-exchange from $K^+$ to $Na^+$. The ion-exchanged seaweed was washed with cold water as above to remove excess salts, then placed in 400 ml of 1% solution (w/v) of potassium chloride (lot #89F-0869, Sigma Chemical Company, St. Louis, Mo.). The suspension was heated in a boiling-water bath at 95° C. for 30 minutes. After 30 minutes, the seaweed was milled in a Waring blender 7010 (model #31BL91). The paste was returned to the boiling- water bath at 95° C. for another 30 minutes. To the paste, 30 g of filter aid was added, stirred, and the mixture filtered using a 1 liter filter bomb fitted with a piece of #54 Whatman filter paper and preheated with boiling distilled water. The collected filtrate was heated to 70° C. and, with stirring, added to 2x volume of 99% isopropyl alcohol warmed to 40° C. The coag was recovered by centrifugation at 3500 rpm for 10 minutes. The pelleted coag was washed in 2x volume of 80% isopropyl alcohol for 45 minutes. The coag was recovered by vacuum filtration through a finely woven nylon cloth, squeezed to remove excess alcohol, and dried at 55° C. in a forced hot-air oven. Once dried, the sample was weighed to determine yield, typically between 30–40%. In the aforementioned example, 7.844 g (39.2% yield) was recovered and then ground through a 40 mesh screen. To isolate the β-carrageenan, the dried product was dissolved in 784 ml distilled water (1% w/v), using heat. While hot (40° C.), 70.5 ml of 25% FMB 451-5 QUAT solution (Huntington Laboratories, Huntington, Ind.), 3% v/v, was added to the extract and then the mixture placed in a 37° C. airdraft incubator for 3 hours. The precipitate which formed was separated by adding 25 g of filter aid and filtering through a preheated 1 liter filter bomb fitted with a piece of #54 Whatman filter paper. A small portion of clear filtrate was checked for additional precipitables by adding a few drops of 25% FMB 451-5 QUAT solution. If and when more precipitate formed, additional FMB 451-5 QUAT solution was added and the solution refiltered. The clear filtrate was heated to 70° C. and, with stirring, added to 2x volume of 99% isopropyl alcohol warmed to 40° C. To this solution, 10% aqueous sodium chloride was added at 1% of the total volume. After several hours, a floc formed. The coag was collected by centrifugation at 3500 rpm for 10 minutes. The coag pellets were washed in 2x volume of 80% isopropyl alcohol for 45 minutes. The coag was recovered by vacuum filtration on a finely woven nylon cloth and squeezed to remove excess alcohol. The coag was then dried at 50° C.. Once dried, the recovered sample weighed 0.64 g (3.2%, based on weight of the weed used). The dried product was ground through a 20 mesh screen. The product was further purified as described in Example 9.

EXAMPLE 12

Use of β-carrageenan as an electrophoresis medium

The separating ability of a β-carrageenan gel as an electrophoretic medium was determined. To prepare a framing gel, a 1% (w/v) SeaKem® LE agarose (FMC BioProducts, Rockland, Me.) solution was prepared by dissolving 0.15 g agarose in 15 ml 1x TAE buffer (40 mM Tris acetate, 1 mM EDTA [pH 8.0]). This was used to cast a gel, 2.3 mm thick, in a mini submarine gel electrophoresis chamber (model #750, Aquebogue Machine Shop, Aquebogue, N.Y.). After the gel had solidified, three of the side lanes were removed by cutting. To fill this space, a 1% (w/v) β-carrageenan solution was prepared by dissolving 0.035 g of the β-carrageenan of Example 9 in 3.5 ml 1x TAE buffer. This solution, while warm was then poured into the agarose framing gel and allowed to cool and solidify. The wells were loaded with 5 microliters (334 ng) of a heat-treated sample of Hind III lambda DNA digest containing bromphenol blue as a tracking dye. Electrophoresis was performed at 35 volts (5 V/cm) for 2 hours. At the end of 2 hours, the gel was removed and stained in an ethidium bromide solution (1 microgram/ml) for 25 minutes, followed by destaining in distilled water for 40 minutes. The gel was examined and photographed under a UV light source (Fotodyne, model 3-4400). Photographs were taken at F4.5, ½ second with a Polaroid® MP-4 Land camera and type 57 4×5 Land™ film. Development time was 20 seconds. The DNA migration was considerably faster in the β-carrageenan than in the agarose framing gel, particularly for the larger fragments.

| DNA FRAGMENT | DISTANCE MIGRATED (mm) | |
|---|---|---|
| SIZE (kB) | 1% AGAROSE | 1.06% β-carrageenan |
| 23.1 | 5.0 | 8.5 |
| 9.4 | 8.5 | 13.7 |
| 6.6 | 10.5 | 15.7 |
| 4.3 | 18.5 | 19.0 |
| 2.3 | 20.5 | 24.0 |

What is claimed is:

1. β-carrageenan in purified form containing less than 2% by weight of sulfate ester.

2. β-carrageenan of claim 1 which contains less than about 1.75% by weight of sulfate ester.

3. β-carrageenan in substantially pure form containing less than 1 % by weight of sulfate ester.

4. β-carrageenan of claim 3 which contains less than about 1% by weight of sulfate ester.

5. β-carrageenan according to claim 1 wherein said purified form is derived from the marine macroalgae *Eucheuma gelatinae* or *Eucheuma speciosa*.

6. β-carrageenan according to claim 2 wherein said purified form is derived from the marine macroalgae *Eucheuma gelatinae* or *Eucheuma speciosa*.

7. β-carrageenan according to claim 3 wherein said purified form is derived from the marine macroalga e *Eucheuma gelatinae* or *Eucheuma speciosa*.

8. β-carrageenan according to claim 4 wherein said purified form is derived from the marine macroalgae *Eucheuma gelatinae* or *Eucheuma speciosa*.

9. β-carrageenan according to claim 1 wherein said purified form is derived from the marine macroalgae *Eucheuma gelatinae*.

10. β-carrageenan according to claim 2 wherein said purified form is derived from the marine macroalga *Eucheuma gelatinae*.

11. β-carrageenan according to claim 3 wherein said purified form is derived from the marine macroalga *Eucheuma gelatinage*.

12. β-carrageenan according to claim 4 wherein said purified form is derived from the marine macroalga *Eucheuma gelatinae*.

13. β-carrageenan according to claim 1 wherein said purified form is derived from the marine macroalga *Eucheuma speciosa*.

14. β-carrageenan according to claim 2 wherein said purified form is derived from the marine macroalga *Eucheuma speciosa*.

15. β-carrageenan according to claim 3 wherein said purified form is derived from the marine macroalga *Eucheuma speciosa*.

16. β-carrageenan according to claim 4 wherein said purified form is derived from the marine macroalga *Eucheuma speciosa*.

* * * * *